United States Patent [19]

Keltner

[11] Patent Number: 4,504,495
[45] Date of Patent: Mar. 12, 1985

[54] PROCESS FOR THE CONTROL OF CHALKBROOD DISEASE IN LEAFCUTTER BEES

[76] Inventor: Lawrence C. Keltner, Cabin Creek Rte., Ismay, Mont. 59336

[21] Appl. No.: 583,381

[22] Filed: Feb. 24, 1984

[51] Int. Cl.³ .................... A01N 37/00; A01N 37/08
[52] U.S. Cl. ..................................... 514/760; 6/12 M
[58] Field of Search ......................... 424/350; 6/12 M

[56] References Cited

U.S. PATENT DOCUMENTS

| | | | |
|---|---|---|---|
| 2,973,298 | 2/1961 | Goldhaft et al. | 424/228 |
| 3,555,055 | 1/1971 | Kaplan | 424/228 |
| 3,954,969 | 5/1976 | Reinert et al. | 424/93 |
| 4,308,627 | 1/1982 | Wallace | 424/228 |

OTHER PUBLICATIONS

Oregon State University Agricultural Experiment Station Bulletin No. 656 (1982), "Inhibition of Chalkbrood Spore Germination in vitro", Stephen et al.

Primary Examiner—Leonard Schenkman
Assistant Examiner—Joseph A. Lipovsky
Attorney, Agent, or Firm—Henderson & Sturm

[57] ABSTRACT

A process for the control of chalkbrood disease among leafcutter bees including the step of fumigating the larva stage of the leafcutter bee with a fungicide in an amount effective to kill or check the growth of spores of the fungus Ascosphaera sp. Where old, previously used beeboards, equipment, grooved boards, shelters, trays, incubators, cell removers, tumblers and other apparatus are used in rearing leafcutter bees, the process further includes the step of fumigating the apparatus.

4 Claims, No Drawings

continued

PROCESS FOR THE CONTROL OF CHALKBROOD DISEASE IN LEAFCUTTER BEES

TECHNICAL FIELD

This invention relates to the process of controlling chalkbrood disease amongst leafcutter bees and more particularly to a process of fumigating the larve stage of the leafcutter bees and the associated rearing equipment with a fungicide effective against the fungus Ascosphaera sp.

BACKGROUND ART

In recent years, the management of cutter bees (Megachilidae family, *Megachile rotundata*) has achieved commerical significance due to the importance of the leafcutter bee in pollination of alfalfa in the western United States.

The leafcutter bees are susceptible to a contagious disease known as chalkbrood, caused by the fungus Ascosphaera sp., which spreads by microscopic spores. The disease has significantly reduced the population of leafcutter bees in certain areas, thus resulting in decreased production and economic losses in the alfalfa seed industry.

Chalkbrood was first identified from populations of *Megachile rotundata* in California in 1973. It has since been recorded from leafcutting bee populations in all states from the Great Plains to the Pacific Coast and all western Provinces of Canada except British Columbia. Not all populations in these areas are diseased but there are few disease-free populations remaining in North America and the incidence of the disease varies greatly from area to area.

The chalkbrood disease turns the body of an infected bee larva into fungal cells which eventually produce millions of spores. The destroyed larvae remaining in the nesting holes is primarily responsible for the transmission of the disease.

Once the disease becomes established in an area it increases rapidly because of the reuse of contaminated nesting media in successive years. Its rapid spread throughout western America is associated with the widespread sale of chalkbrood-contaminated boards and/or the use of such boards for trapping of endemic bee populations in disease-free areas. The disease is spread through local populations by adult bees emerging from contaminated media. It has been shown that a single adult bee may carry from 50 to 300 million spores on its body surface after having chewed through a single diseased cadaver as it extracts itself from the cell or nesting material.

Over the past several years various control measures have been developed but none have been completely effective or economically practical. Sterilization of nesting media has been attempted by use of dry chlorine or bleach, convection heat, and microwave exposure. Also, surface sterilization of adult bees consisting of a bee bath in sodium hypochlorite or iodine has been employed. Dusting with general antibiotics and fungicides in such a manner that they are ingested by the adult bee also has met with little success.

Those concerned with the control of chalkbrood disease in leafcutter bees recognize the need for an improved method to effectively and economically control the disease.

DISCLOSURE OF THE INVENTION

The present invention provides an inexpensive and practical method for the prevention of chalkbrood disease amongst bees of the family Megachilidae. The process has been carried out with great success by exposing the prepupal or overwintering diapause stage of the leafcutter bee and all related equipment to a penetrating fumigant or fungicide in an amount effective to kill or check the growth of spores of the fungus Ascosphaera sp.

An object of the present invention is to provide an improved method for the control of chalkbrood disease in leafcutter bees.

Another object of the present invention is the provision of a method for the control of chalkbrood disease which is practical and inexpensive to practice.

A further object of the present invention is to provide a method for the control of chalkbrood disease which is highly effective.

Other objects, advantages and novel features of the present invention will become apparent from the following description of the best mode for carrying out the invention.

BEST MODE FOR CARRYING OUT THE INVENTION

Previous attempts to control chalkbrood disease in leafcutter bees have met with failure because of a failure to understand the mechanism by which the disease is transmitted. A background knowledge is helpful in understanding the new and useful process in the control of chalkbrood disease.

When the female leafcutter bee emerges, she mates, feeds, chooses her nesting site, and then begins to make cells and provision them. She makes cells with cuttings from leaves or petals because she has no glands that produce wax. After she has made the walls with oblong leaf cuttings, she fills the cell about two-thirds full with pollen and nectar, and then lays an egg, which floats on the nectar pool. She builds cells end to end in the tunnel, beginning at the back and ending near the entrance (capping each cell with circular leaf cuttings), and then she plugs the tunnel entrance with closely packed circular leaf cuttings.

The egg hatches in its cell, and the larva feeds on the pollen and nectar. The larva sheds its skin several times as it grows, passing through the five larval life stages or instars. It is at this stage where if the pollen and nectar had been contaminated with chalkbrood fungus spores from the adult bee body, that the succeeding generations will have contracted chalkbrood disease and become a cadaver.

Until it is full grown the larva has a blind gut and, therefore, cannot defecate and thus contaminate its food and quarters. After eating all its food, the larva places its dry, fecal pellets beneath the cap at the end of the cell and separates itself from this contamination by spinning a tough, silken cocoon. The full-grown larva spends the winter in its cocoon, this is referred to as the prepupal or overwintering diapause (resting) stage (it is unproven that these two stages are one in the same). Apparently the blind gut stage is the only time the bee is affected by chalkbrood disease.

By negating the chalkbrood fungus spore at the prepupal or diapause stage, the healthy bee emerges and is not contaminated by chalkbrood disease, thus breaking the chain that connects chalkbrood disease from one generation to the next.

The following Examples are illustrative of the best mode for carrying out the invention. They are, obviously, not to be construed as limitative of the invention since various other embodiments can readily be evolved in view of the teachings provided herein.

EXAMPLE 1

The initial test was with a gallon (10,000 live bee count) of leafcutter bee cells in the prepupal stage and that had a Montana State Lab test of 3.2% chalkbrood. This sample was split in half, half were frozen (to indicate diapose) and the other half left unfrozen. Both halves were exposed to a penetrating fumigant or fungicide, 680 grams of the chemical methyl bromide, for a period of three minutes to one hour in an enclosure consisting of approximately one cubic yard. After removal from the enclosure the cells were aired with a 24" portable house fan for 30 minutes to eliminate the remaining chemical. The bees were then incubated at a temperature of 80° F. for 14 days and then checked for livability. The tests of three to 15 minutes for the unfrozen cells and of 10 to 25 minutes for the frozen cells appears to be the optimum exposure for this amount and type of chemical to produce a livable sample. It is to be understood that fungicides other than methyl bromide can be used so long as the fungicide is used in an amount effective to kill or check the growth of spores of the fungus Ascosphaera sp.

EXAMPLE 2

The 15 minute frozen cell sample of Example 1 was put in an isolated alfalfa field and allowed to nest. Ninety days later, the new cells were removed from the nest and sent to the Idaho State bee lab for testing. The test from Idaho State bee lab indicated there was 0.48% chalkbrood. This was approximately six times lower than the original sample.

It is readily apparent that the frozen or unfrozen cells, the different exposure times, the amount of chemical, and the type of penetrating fumigant or fungicide all have a correlating factor in the livability of the bees and the amount of chalkbrood eliminated.

EXAMPLE 3

All of the bee rearing equipment was put in an enclosure and exposed for 24 hours at the rate of 680 grams of methyl bromide per 1,000 cubic feet, thus ensuring no recontamination from this source. This step can be considered either an entity or an intricate part of the process depending on the amount of chalkbrood to be eliminated.

The above description and examples indicate that treatment of the larva stage of the leafcutter bee by a penetrating fumigant or fungicide effective against the fungus Ascosphaera sp., together with the treatment of all bee rearing equipment, is an inexpensive, practical and effective method of controlling chalkbrood disease in leafcutter bees.

Thus, it is apparent that at least all of the stated objectives of the present invention have been achieved.

Obviously, many modifications and variations of the present invention are possible in light of the above teachings. It is therefore to be understood that, within the scope of the appended claims, the invention may be practiced otherwise than as specifically described.

I claim:

1. A process for controlling chalkbrood disease in leafcutter bees, comprising the step of:
    fumigating the larva stage of the leafcutter bee with an amount of methyl bromide effective against the fungus Ascosphaera sp.

2. The process of claim 1 wherein said methyl bromide is applied in an amount of about 140 grams per 1,000 leafcutter bee larvae.

3. The process of claim 2 wherein said fumigation is continued from about three minutes to about 60 minutes.

4. The process of claim 3 wherein said fumigation is continued from about 10 minutes to about 25 minutes.

* * * * *